United States Patent [19]

Hertel et al.

[11] Patent Number: 4,914,028
[45] Date of Patent: Apr. 3, 1990

[54] METHOD OF PREPARING BETA-2′,2′-DIFLUORONUCLEOSIDES

[75] Inventors: Larry W. Hertel; Cora Sue Grossman; Julian S. Kroin, all of Indianapolis, Ind.

[73] Assignee: Eli Lilly and Company, Indianapolis, Ind.

[21] Appl. No.: 159,792

[22] Filed: Feb. 10, 1988

[51] Int. Cl.$^4$ .................. C12P 19/40; C12N 9/06; C07H 19/36
[52] U.S. Cl. .................. 435/88; 435/191; 435/280; 536/24; 536/26
[58] Field of Search .................. 536/124, 26; 435/227, 435/280, 88, 19

[56] References Cited

U.S. PATENT DOCUMENTS 4,526,988 7/1985 Hertel .................. 549/313
4,692,434 9/1987 Hertel .................. 514/49

FOREIGN PATENT DOCUMENTS 0002192 6/1979 European Pat. Off. .............. 514/45
184365 6/1986 European Pat. Off. .
211354 2/1987 European Pat. Off. .

OTHER PUBLICATIONS

Montgomery et al., *J. Med. Chem.* 29, 2389–2392 (1986).
Bennett et al., *Mol. Pharmacol.* 12, 242–250 (1976).
Secrist et al., *J. Med. Chem.* 30, 746–749 (1987).
Vorbruggen et al, the Chemical Abstracts 92: 198686u (1980).
Vorbruggen et al, Liebigs Ann. Chem pp. 745–761 (1976).

*Primary Examiner*—Herbert J. Lilling
*Attorney, Agent, or Firm*—Joseph A. Jones; Leroy Whitaker; Bruce J. Barclay

[57] ABSTRACT

A process for preparing β-2′,2′-difluoronucleosides, and a novel intermediate thereto, are disclosed.

2 Claims, No Drawings

METHOD OF PREPARING BETA-2',2'-DIFLUORONUCLEOSIDES

Background of the Invention

U.S. Pat. Nos. 4,526,988 and 4,692,434 disclose a class of 2',2'-difluoronucleosides having excellent activity as antiviral agents. EPO Application No. 85308547.0 discloses the use of the same and related compounds as oncolytic agents. Both disclosures teach that the β-difluoronucleosides are preferred because of their increased biological activity as compared to the corresponding α-isomers.

The two disclosures teach the isolation of the difluoronucleosides by a multi-step synthetic route which is difficult to reproduce in preparing large quantities of the desired compound. These procedures are relatively low yielding. The β-difluoronucleosides are isolated by laborious and time consuming column chromatography procedures.

The present invention provides an efficient process for preparing certain of the foregoing β-difluoronucleosides from a mixture of α- and β-isomers.

Summary of the Invention

The present invention relates to a process for preparing the β-isomer of a compound of the formula

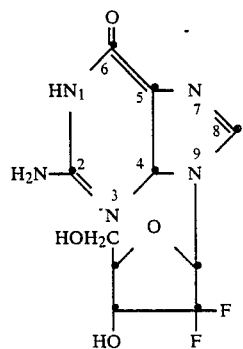

I comprising treating the racemic mixture of a compound of the formula

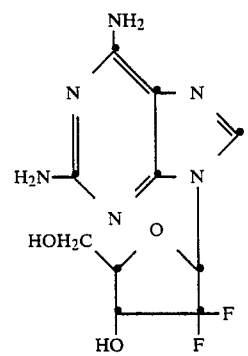

II with adenosine deaminase.

The present invention also provides a process for preparing the β-isomer of a compound of the formula

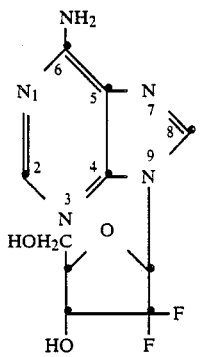

III comprising treating a racemic mixture of a compound of Formula III with adenosine deaminase to provide the β-isomer of a compound of the formula

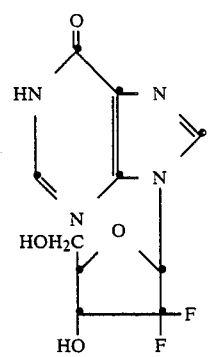

IV which is subsequently aminated.

The present invention also provides the β-isomer of a compound of the formula

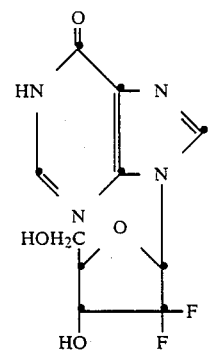

IV

Detailed Description of the Invention

According to the processes of the present invention, a catalytic to approximately an equimolar or excess amount of adenosine deaminase is added to a solution of the appropriate purine starting material in a suitable solvent. While a variety of solvents may be used, preferred solvents include the polar solvents such as the alcohols or water, which is preferred. The reaction is substantially complete after about 10 minutes to about 12 hours when conducted at a temperature in the range of about 0° C. to about 100° C. The reaction is preferably conducted for approximately 1 to 4 hours at a temperature in the range of about 20° C. to about 25° C.

If the foregoing reaction is allowed to proceed beyond the approximate maximum time indicated, the quantity of α-isomer produced will increase accordingly. Therefore, in order to maximize the amount of β-isomer synthesized it is preferred to follow the progress of the reaction according to procedures well known to one of ordinary skill in the art such as high performance liquid chromatography or thin layer chromatography.

Conversion of the 6-oxopurine intermediate of Formula IV to the 6-aminopurine of Formula III is carried out by standard amination conditions. For example Vorbrüggen et al. in Liebigs Ann. Chem. 745–761 (1976) disclose the synthesis of a 6-oxopurine to a 6-aminopurine by first blocking all available oxygen atoms with a trimethylsilyl protecting group and aminating with ammonia and hydrolyzing the resulting intermediate with acid. The reaction is preferably conducted in the presence of a mutual organic solvent for a period of about 10 minutes to about 120 hours when conducted at a temperature in the range of about 0° C. to about 150° C.

The desired β-difluoronucleoside prepared by either process is readily isolated by standard techniques. The compound may be isolated by either extracting the desired compound into an organic solvent or, preferably, collecting the precipitated solid by vacuum filtration. The desired compound may be further purified if desired by any standard technique such as crystallization from common solvents or column chromatography over solid supports such as silica gel or alumina, and especially $C^{18}$ high performance liquid chromatography. However, one advantage of the present invention is that such additional purification techniques are not needed because the compound is first isolated in substantially pure form.

The compounds prepared by the process of the present invention are taught as antiviral agents in U.S. Pat. Nos. 4,526,988 and 4,692,434, herein incorporated by reference. These patents also disclose methods of preparing the compounds which are starting materials in the present process.

Adenosine deaminase is a naturally occurring substance which converts adenosine to inosine in the biochemical pathway of higher animals by the degradation of purines to nitrogenous excretory products. Adenosine deaminase is commercially available and is most commonly isolated from various mammalian tissues including calf or bovine intestine or spleen. All types of adenosine deaminase are believed suitable for use in the process of the present invention. However, Type I adenosine deaminase is preferred for such use.

The following Example further illustrates the process of the present invention. The Example is not intended to be limiting to the scope of the invention in any respect and should be so construed.

EXAMPLE 1

Synthesis of β-1-(2-amino-6-oxo-1H,9H-purine-9-yl)-2-desoxy-2,2-difluororibose 1-(2,6-Diamino-9H-purin-9-yl)-2-desoxy-2,2-difluororibose (0.75 g, 2.48 mmol) was dissolved in 90 ml of water and 100 mg of adenosine deaminase was added to the mixture. The solution was stirred at room temperature for approximately two hours and stored in the refrigerator overnight. The precipitated solid was collected by vacuum filtration to provide 0.26 g of the desired compound β-1-(2-amino-6-oxo-1H,9H-purin-9-yl)-2-desoxy-2,2-difluororibose.

---

H-NMR (300 MH$_z$, DMSO-d$_6$): δ3.65 (m, 2H, 5'-H), 3.85 (m, 1H, 4'-H), 4.38 (m, 1H, 3'-H), 5.2 (t, 1H, 5'-OH), 5.97 (dd, 1H, 1'-H), 6.30 (d, 1H, 3'-OH), 6.55 (bs, 2H, 2-NH$_2$), 7.89 (S, 1H, 8-H). Mass spectrum = 303 (parent ion)

---

We claim:

1. A process for isolating the β-diastereomer of a compound of the formula

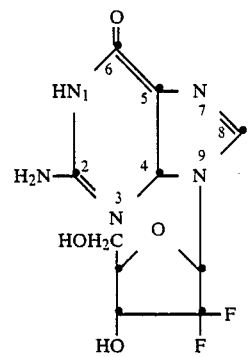

comprising treating a racemic mixture of a compound of the formula

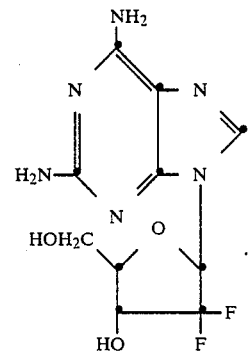

with adenosine deaminase, and recovering the β-diastereomer as a solid from the reaction mixture.

2. A process for preparing the β-diastereomer of a compound of the formula

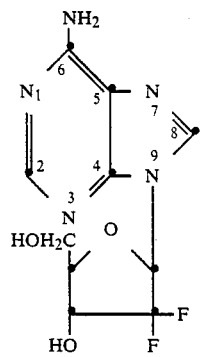

comprising treating a racemic mixture of a compound of Formula III with adenosine deaminase to provide the β-diastereomer of a compound of the formula
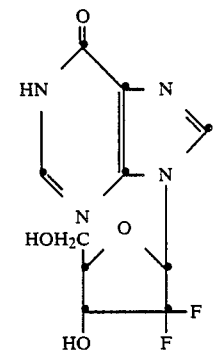
which is recovered as a solid from the reaction mixture, and subsequently aminated.
* * * * *